United States Patent [19]

Fillion et al.

[11] Patent Number: 5,173,600
[45] Date of Patent: Dec. 22, 1992

[54] APPARATUS FOR DETECTING IMPURITIES IN A FLUID CIRCUIT USING OPTICAL FIBERS AND A MAGNET

[75] Inventors: Jean-Claude Fillion, Paris; Pascal Makowski, Thomery; Anne Thenaisie, Villeparisis, all of France

[73] Assignee: Societe Nationale d'Etude et de Construction de Moteurs D'Aviation (S.N.E.C.M.A.), Paris, France

[21] Appl. No.: 765,931

[22] Filed: Sep. 26, 1991

[30] Foreign Application Priority Data

Sep. 26, 1990 [FR] France .................. 90 11843

[51] Int. Cl.⁵ ............................................. H01J 5/16
[52] U.S. Cl. ................................. 250/227.11; 250/573
[58] Field of Search ................. 250/227.11, 573–576; 356/436, 441, 442

[56] References Cited

U.S. PATENT DOCUMENTS

| | | |
|---|---|---|
| 3,647,300 | 3/1972 | Skala ................................. 250/574 |
| 4,349,734 | 9/1982 | DiGuiseppi ..................... 250/227.11 |
| 4,851,666 | 7/1989 | Anderson et al. ............. 250/227.11 |
| 4,899,047 | 2/1990 | Cry et al. ....................... 250/227.11 |
| 5,122,655 | 6/1992 | Hornung et al. ..................... 250/573 |

Primary Examiner—David C. Nelms
Assistant Examiner—S. Allen
Attorney, Agent, or Firm—Bacon & Thomas

[57] ABSTRACT

The apparatus for detecting impurities in a fluid circuit has a body member associated with a fluid conduit or reservoir which defines a detection zone. A magnet is associated with the body member and communicates with the fluid in the detection zone to attract metallic impurities. Fiber optic members extend from opposite sides of the detection zone, with one of the fiber optic members associated with a light source and the other fiber optic member associated with a light sensor. The light is transmitted by the first fiber optic member into the fluid in the detection zone. The light passing through the fluid is transmitted by the second fiber optic member to the light sensor.

13 Claims, 3 Drawing Sheets

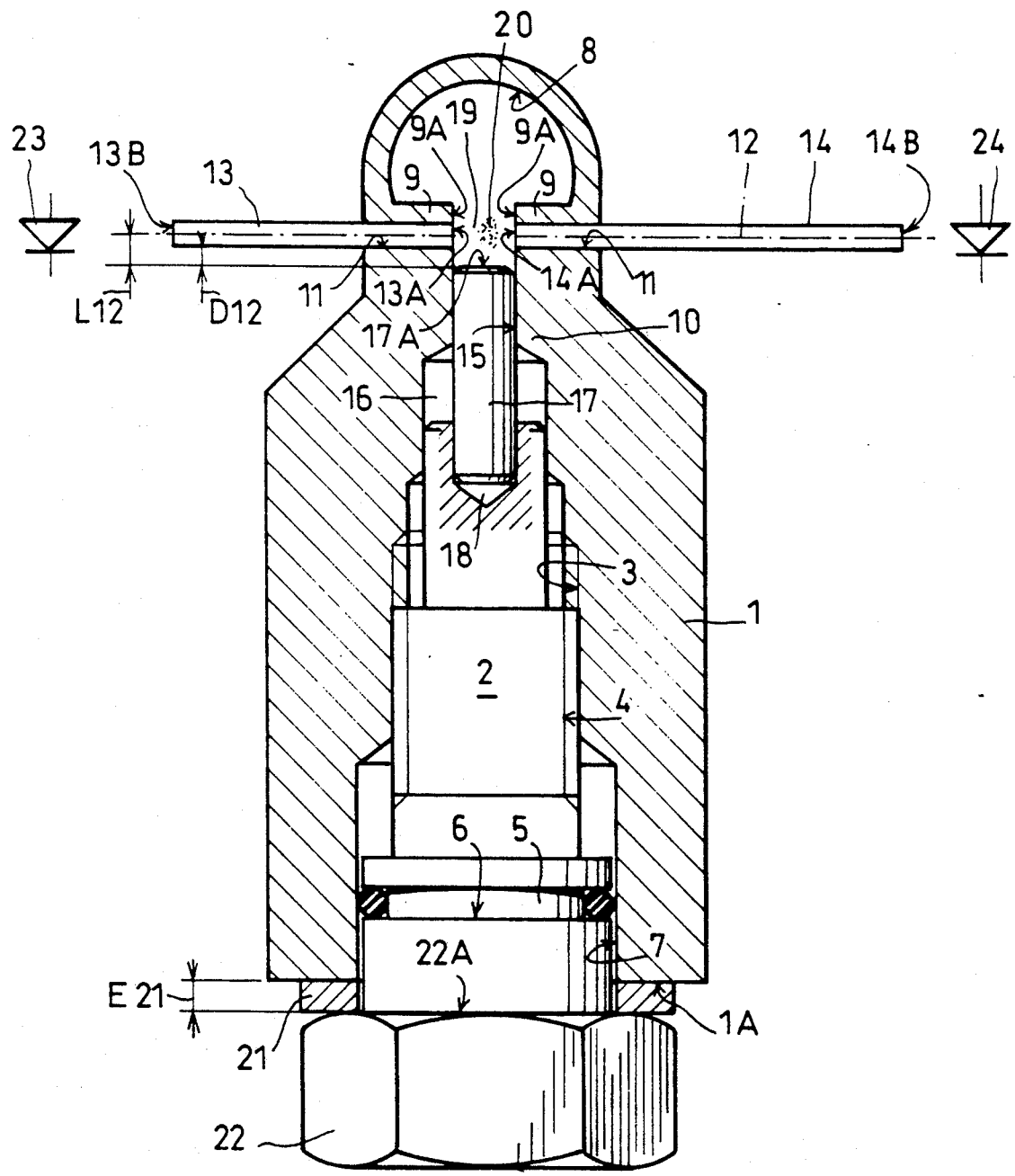
fig_1

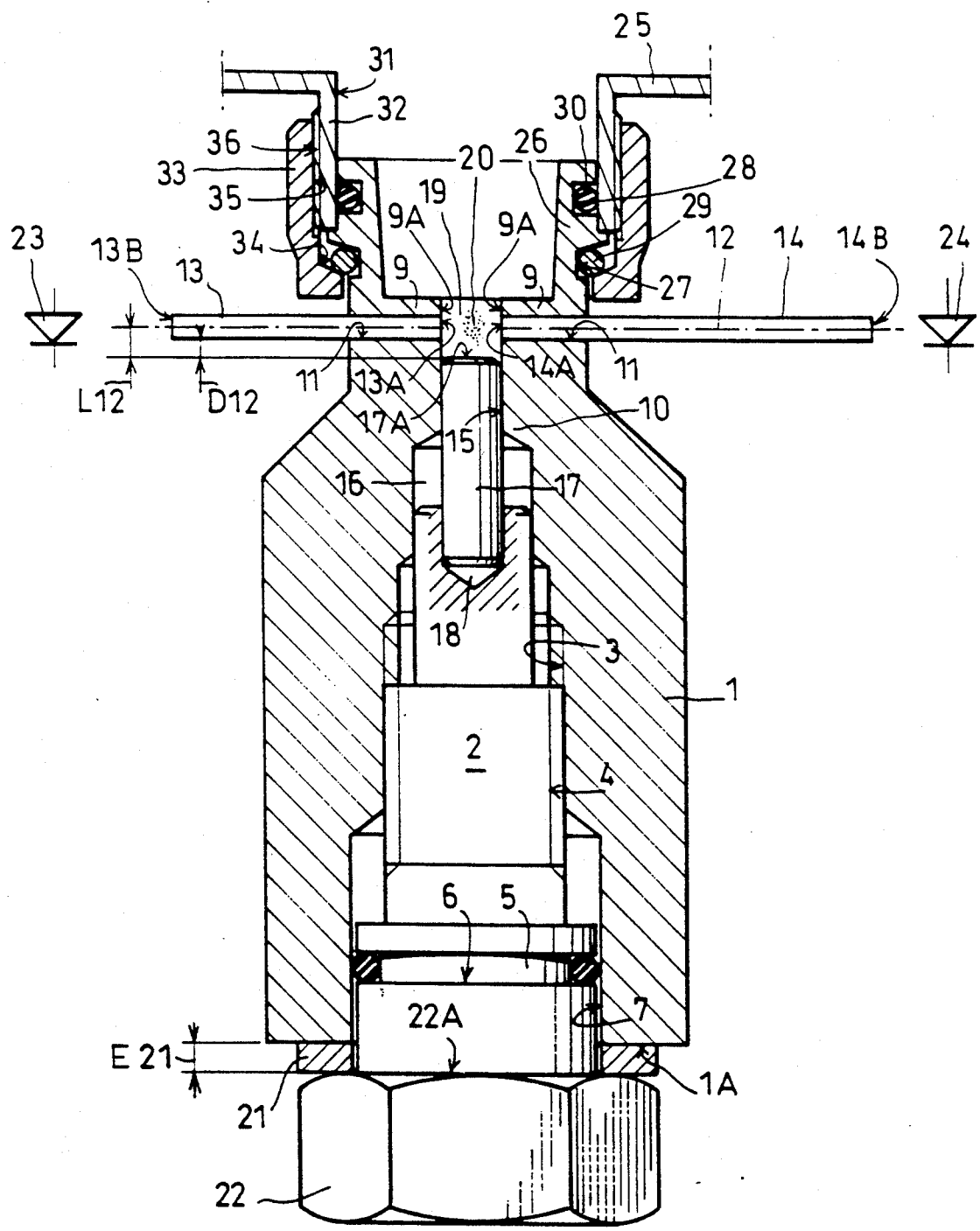
fig_2

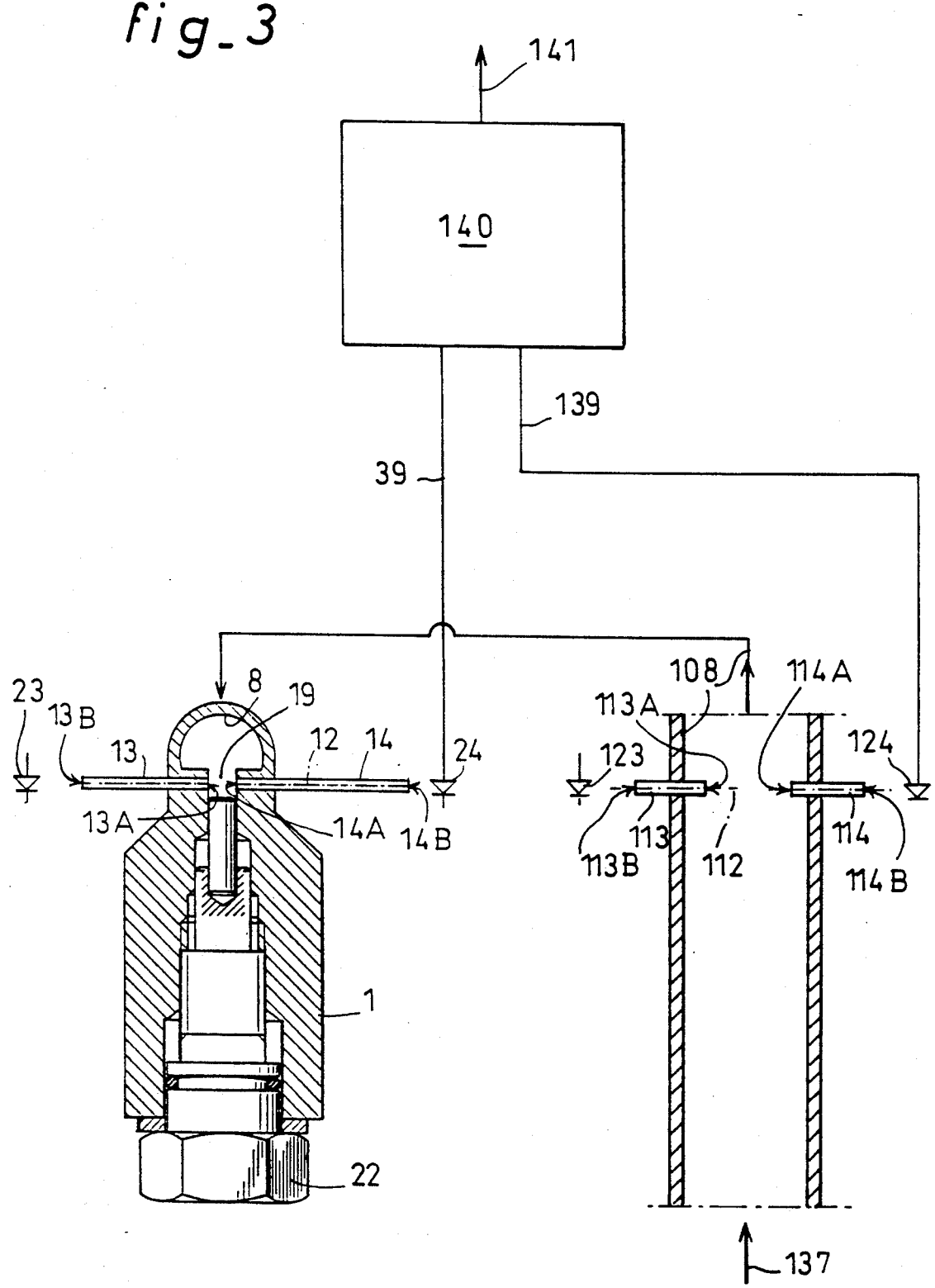
fig_3

APPARATUS FOR DETECTING IMPURITIES IN A FLUID CIRCUIT USING OPTICAL FIBERS AND A MAGNET

BACKGROUND OF THE INVENTION

The control of the quality of a fluid in a circuit, such as a lubrication circuit for machinery, is essential in order to keep the operating parts of the machinery in proper working order.

Devices for detecting the presence of impurities in the fluid are used to maintain the quality of the fluid. Typically, the devices monitor the transparency of the fluid in order to detect any impurities. It is also known to incorporate magnets into these devices to attract metallic impurities. An electrical circuit, the conductivity of which is effected by the presence of the metallic impurities, is used to monitor the presence of the impurities and to activate an alarm or other signal when the impurities reach a predetermined level. While such devices have proved successful, the complexity of the electric circuits utilized raise the cost of the devices and reduce their reliability.

SUMMARY OF THE INVENTION

The apparatus for detecting impurities in a fluid circuit according to the present invention has a body member associated with a fluid conduit or reservoir and defines a detection zone. A magnet is associated with the body member and communicates with the fluid in the detection zone to attract metallic impurities. Fiber optic members extend from opposite sides of the detection zone, with one of the fiber optic members associated with a light source and the other fiber optic member associated with a light sensor. The light is transmitted by the first fiber optic member into the fluid in the detection zone. The light passing through the fluid is transmitted by the second fiber optic member to the light sensor.

The ends of the fiber optic members extend through openings defined by the body member, which openings are axially aligned on opposite sides of the detection zone.

The magnet may be attached to a stopper member which is removably engaged with the body member. A spacing washer is utilized between the stopper member and the body to adjust the position of the end of the magnet with respect to the ends of the fiber members and the coaxial openings.

The invention also encompasses a hydraulic circuit utilizing a pair of fiber-optic, impurity detecting devices. One of the detecting devices is associated with a conduit for feeding a purified fluid into the fluid circuit. The second detector is associated with a conduit which directs the fluid after it has been utilized in fluid actuated devices. The light sensors of each of the detectors are connected to a comparator which compares the signals emitted from each of the light sensors. The signal from the first detector provides a base against which the fluid in the second conduit is compared. Any difference between the signals is due to the presence of the impurities in the fluid passing through the second detector.

The device according to the invention utilizes fiber optic members to detect the presence of impurities in the fluid. The fiber optic members may be connected to remote readouts and remote detection indicators simply by fiber optic transmission. Thus, the complex electric circuits of the known devices are eliminated.

BRIEF DESCRIPTION OF THE DRAWINGS

FIG. 1 is a cross-sectional view of a first embodiment of the detector according to the present invention.

FIG. 2 is a cross-sectional view of a second embodiment of the detector according to the present invention.

FIG. 3 is a schematic representation of a hydraulic circuit according to the present invention incorporating two impurity detectors.

DETAILED DESCRIPTION OF THE PREFERRED EMBODIMENTS

FIG. 1 discloses a impurities detector having a body member 1 defining a generally centrally located bore having internal threads 3 which cooperate with the external threads 4 of stopper member 2. The interengaging threads 3 and 4 serve to removably attach the stopper member 2 to the body member 1.

A seal 5, such as in O-ring seal or the like, is located in circumferential channel 6 on the stopper member 2 such that it seals against the inner surface 7 of the bore defined by the body member 1.

A fluid conduit 8 is rigidly joined to the body member 1. The body member defines opposite walls 9 and an inner connecting third wall 10. A pair of co-axial tubular openings 11 are defined by the body member and extend along axis 12 such that the openings 11 open through opposite walls 9. The openings face into a detection zone 19 which is located between the inner, facing surfaces 9A of the walls 9.

Fiber optic members 13 and 14 are affixed in the tubular openings 11 and sealed such that fluid may not leak past the fiber optic members and out of the body member. The end surfaces 13A and 14A of the fiber optic members 13 and 14 are illustrated as being co-planar with the inner surfaces 9A of walls 9. However, it is to be understood that the end surfaces 13A and 14A could be displaced away from surfaces 9A of the walls 9 without exceeding the scope of this invention.

Third wall 10 defines a hole 15 which connects the opening 16, formed in body member 1, with the detection zone 19, which zone communicates with the interior of conduit 8. A generally cylindrical, permanent magnet 17 has a first end fitted into the hole 15 with minimal clearance between the magnet and the inner surface of the hole 15. The pole end face 17A of the magnet 17 faces into and communicates with the detection zone 19. The end face 17A is displaced away from the axis 12 of the openings 11 by a distance L12 and from the nearest portion of the openings 11 by a distance D12. Thus, it can be seen that the detection zone 19, in regard to the conduit 8, constitutes a decanting well for the impurities 20. Metallic impurities are also attracted into the detection zone 19 by the pole end face 17A of the permanent magnet 17.

A spacer washer 21, having a thickness E21, is interposed between the body member 1 and a clamping surface 22A of the head 22 formed on stopper member 2 in order to adjust the distances L12 and D12, and, hence, the level of impurities which will activate the alarm.

A light source 23 is operatively associated with the second 13B of fiber optic member 13 and a light sensor 24 is operatively associated with the second end 14B of fiber optic member 14. The light transmitting properties of the fiber optic members transmit the light from light source 23, into the detection zone 19, from the detection zone 19 and onto the light sensor 24. Ends 13B and 14B of the fiber optic members may be displaced away from the body member 1 and the fluid circuit, such as in the case of aircraft display screens or automobile dashboards.

FIG. 2 illustrates a second embodiment of the invention which is similar to the previously described embodiment, except for its attachment to a reservoir or conduit. In this embodiment, the detection zone 19 communicates with an engine oil case 25. In order to attach the body member 1 to the engine oil case 25, a fastener bush 26, formed on the body member 1 and defining outer circumferential grooves 27 and 28, and a connector 33 are utilized. A metal retainer ring 29 is located in groove 27, while a seal 30, such as an O-ring seal, is located in groove 28 to seal against the inner surface of flange 32. The connector 33 has a shoulder 34 and threads 35 which engage threads 36 formed on the flange 32. As can be seen, flange 34 bears against retainer ring 29 as the connector 33 is threaded onto flange 32 to attach the body member 1 to the engine oil case 25. All other aspects of the second embodiment are identical to those of the first embodiment, previously described.

FIG. 3 schematically illustrates a fluid circuit utilizing a pair of fiber-optic detectors to detect impurities in the fluid passing through the circuit. A first conduit 108 is connected between a conduit 137 from a fluid reservoir and the operational circuit and passes purified fluid from the reservoir into the operating circuit.

A first impurity detector is operatively associated with conduit 108 and includes fiber optic members 113 and 114 extending through opposite sides of the conduit 108 such that inner ends 113A and 114A are co-axial along axis 112. Ends 113B and 114B are respectively operatively associated with a light source 123 and a light sensor 124. Light sensor 124 is operatively connected to a comparator 140 via lead 139. Comparator 140 is also connected to light sensor 24 of a second detector via lead 39.

The second detector may be either of the embodiments previously described, although the first embodiment is illustrated in FIG. 3. This detector is associated with a conduit through which the fluid passes after it has been used to lubricate, actuate, or otherwise interact with the devices of the operational circuit.

When the fluid in conduit 8 contains little or no impurities, its transparency is very similar to the transparency of the purified input fluid passing through conduit 108. Thus, the light signal emitted by light source 23 and transmitted through the fiber optic members 13 and 14 to light sensor 24 will be very similar to the signal transmitted by light sensor 124. However, the accumulation of impurities in detection zone 19 will attenuate the light signal emitted from end 13A of fiber optic member 13 and received by end 14A of fiber optic member 14. Thus, the light sensor 24 generates an attenuated signal significantly different from the signal generated by light sensor 124. Thus, comparator 140 may detect this difference and generate an output signal 141 to activate an alarm, a warning light or the like. This will provide an indication to the operator that it is necessary to change the filter in the fluid system, or to replace the contaminated fluid.

The thickness E21 of spacer washer 21 allows the adjustment of the depth of the detection zone 19, as well as the adjustment of distances L12 and D12 separating the pole face 17A of the magnet 17 from the fiber optic members 13 and 14.

Although the illustrated embodiments show the ends 13A and 14A of the fiber optic members being co-planar with the inner surfaces 9A of the walls 9, it can be appreciated that the ends 13A and 14A may be displaced away from the surfaces 9A. In this instance, a transparent material (such as glass or the like) may be inserted into the openings 11 between the ends 13A and 14A, and the inner surfaces 9A. If the transparent body is sealed to the body member in the openings 11, the fiber optic members 13 and 14 need not be sealed in the openings 11.

The light sensor 24 may be combined with an alarm to notify the user when the maximum amount of impurities have been accumulated in the detection zone 19.

If the impurities 20 in the fluid are non-metallic, the magnet 17 need not be utilized. The impurities detector will still sense the impurities in the detection zone 19 just as effectively and the detector allows monitoring of the fluid purity. Obviously, a non-magnetic member must be utilized to seal the opening 15.

The advantages of the device according to the present invention include the ability to move the light source and light sensor far from the fluid circuit through the use of fiber optic members; adjustment of the alarm level by using different spacer washers; permanent monitoring of the fluid in the circuit; and lack of interference in the detection capabilities caused by nuclear or magnetic interference.

The differential comparator 140, illustrated in FIG. 3, receives the data relating to light-intensity measurements transmitted from light sensors 24 and 124 and measures the difference between them. The comparator 140 takes into account the inherent opacity of the purified fluid and subtracts it from the operation fluid passing through conduit 8. The differential signal 141 corresponds solely to the attenuation in transmission caused by the impurities and is not effected by the opacity of the purified fluid.

The foregoing description is provided for illustrative purposes only and should not be construed as in any way limiting this invention, the scope of which is defined solely by the appended claims.

We claim:

1. A detector for detecting the presence of impurities in a fluid comprising:

a) a body member having opposite first and second facing walls and an interconnecting third wall defining a detection zone into which flows at least a portion of the fluid, the walls defining first and second co-axial openings opening into the detection zone;

b) a first fiber optic member having a first end disposed in the first opening and a second end operatively associated with a light source such that light from the source is transmitted by the first fiber optic member into the fluid in the detection zone;

c) a second fiber optic member having a first end disposed in the second opening and a second end operatively associated with a light sensor such that the light emitted by the first end of the first fiber optic member and passing through the fluid in the detection zone is transmitted by the second fiber optic member to the light sensor; and, d) a magnet located in the third wall such that a pole on a first end of the magnet faces into and communicates with the detection zone, the first end being displaced from an axis of the first and second opening.

2. The detector of claim 1 wherein the third wall defines a seat opening into the detection zone and wherein the least a portion of the magnet extends into the seat.

3. The detector of claim 1 further comprising:
a) a stopper member having the magnet attached thereto; and,
b) means to removably attach the stopper member to the body member.

4. The detector of claim 3 wherein the means to removably attach the stopper member to the body member comprises inter-engaging threaded portions formed on the stopper member and the body member.

5. The detector of claim 1 further comprising a fluid conduit defined by the body member such that the fluid conduit communicates with the detection zone.

6. The detector of claim 1 further comprising means to removably attach the body member to a fluid reservoir.

7. The fluid detector of claim 6 wherein the means to removably attach the body member to a fluid reservoir comprises:
a) a fastener bush associated with the body member;
b) a connector member operatively associated with the fastener bush and adapted to be connected to the fluid reservoir.

8. The detector of claim 3 wherein the stopper member includes a headed portion extending exteriorly of the body member and further comprising a spacer washer interposed between the headed portion and the body member so as to position the first end of the magnet a predetermined distance from an axis of the first and second openings.

9. A system for detecting impurities in a fluid circuit including at least a first conduit for feeding fluid into the fluid circuit and a second conduit, comprising:
a) a first detector operatively associated with the first conduit, the first detector comprising;
  i) a first fiber optic member having a first end operatively associated with the first conduit and a second end operatively associated with a light source such that light from the light source is transmitted by the first fiber optic member into the first conduit;
  ii) a second fiber optic member having a first end associated with the first conduit in substantial alignment with the first end of the first fiber optic member and a second end operatively associated with a first light sensor such that light emitted by the first fiber optic member and passing through the fluid in the first conduit is transmitted by the second fiber optic member to the first light sensor;
b) a second detector operatively associated with the second conduit, the second detector comprising:
  i) a body member having opposite first and second facing walls and an interconnecting third wall defining a detection zone into which flows at least a portion of the fluid, the walls defining first and second co-axial openings opening into the detection zone;
  ii) a first fiber optic member having a first end disposed in the first opening and a second end operatively associated with a light source such that light from the source is transmitted by the first fiber optic member into the fluid in the detection zone;
  iii) a second fiber optic member having a first end disposed in the second opening and a second end operatively associated with a light sensor such that the light emitted by the first end of the first fiber optic and passing through the fluid in the detection zone is transmitted by the second fiber optic member to the light sensor; and,
  iv) a magnet located in the third wall such that a pole on a first end of the magnet faces into and communicates with the detection zone, the first end being displaced from an axis of the first and second openings; and,
c) comparator means operatively connected to the first and second light sensors to measure the difference between the light intensities of the first and second light sensors.

10. The system of claim 9 wherein the third wall of the second detector defines a seat opening into the detection zone and wherein the least a portion of the magnet extends into the seat.

11. The system of claim 9 further comprising:
a) a stopper member having the magnet attached thereto; and,
b) means to removably attach the stopper member to the body member of the second detector.

12. The system of claim 11 wherein the means to removably attach the stopper member to the body member of the second detector comprises inter-engaging threaded portions formed on the stopper member and the body member.

13. The system of claim 11 wherein the stopper member includes a headed portion extending exteriorly of the body member and further comprising a spacer washer interposed between the headed portion and the body member so as to position the first end of the magnet a predetermined distance from an axis of the first and second openings.

* * * * *